(12) United States Patent
Lin (10) Patent No.: US 8,900,515 B2
(45) Date of Patent: Dec. 2, 2014

(54) BIOSENSING DEVICE

(75) Inventor: Meng Yi Lin, Taipei (TW)

(73) Assignee: Health & Life Co., Ltd., Taipei (TW)

( * ) Notice: Subject to any disclaimer, the term of this patent is extended or adjusted under 35 U.S.C. 154(b) by 227 days.

(21) Appl. No.: 13/304,541

(22) Filed: Nov. 25, 2011

(65) Prior Publication Data

US 2012/0101737 A1    Apr. 26, 2012

Related U.S. Application Data

(63) Continuation-in-part of application No. 12/054,896, filed on Mar. 25, 2008, now abandoned.

(51) Int. Cl.
| | | |
|---|---|---|
| G01N 27/00 | (2006.01) | |
| G01N 33/487 | (2006.01) | |
| G01N 27/416 | (2006.01) | |
| G01N 27/26 | (2006.01) | |
| G01N 27/414 | (2006.01) | |

(52) U.S. Cl.
CPC ... G01N 33/48771 (2013.01); *B01L 2300/0825* (2013.01); *G01N 27/4163* (2013.01); *G01N 27/26* (2013.01); *G01N 27/4148* (2013.01); *Y10S 436/805* (2013.01); *Y10S 436/809* (2013.01)

USPC .......... 422/82.01; 422/52; 422/68.1; 422/73; 422/82.05; 422/82.06; 422/82.07; 422/82.08; 422/82.09; 422/82.11; 422/407; 422/501; 422/520; 422/503; 422/504; 422/507; 436/164; 436/177; 436/43; 436/63; 436/149; 436/172; 436/174; 436/518; 436/805; 436/809; 435/29; 435/4; 435/7.1

(58) Field of Classification Search
CPC .............. G01N 33/48771; G01N 27/4163; B01L 2300/0825
USPC .......... 422/52, 68.1, 73, 82.01, 82.05, 82.06, 422/82.07, 82.08, 82.09, 82.11, 407, 501, 422/502, 503, 504, 507; 436/164, 177, 43, 436/63, 149, 172, 174, 518, 805, 809; 435/29, 4, 7.1

See application file for complete search history.

(56) References Cited

U.S. PATENT DOCUMENTS 5,873,990 A * 2/1999 Wojciechowski et al. .... 204/406

* cited by examiner

*Primary Examiner* — Dennis M White
(74) *Attorney, Agent, or Firm* — WPAT, P.C.; Anthony King (57) ABSTRACT

The present invention provides a biosensing device, comprising an input unit, an analysis unit, a process unit, and a set unit for storing resulting data values as the basis for calibrating the biosensing device, to set up the calibration parameters of a strip of the biosensing device.

3 Claims, 8 Drawing Sheets

BIOSENSING DEVICE

FIELD OF THE INVENTION

The invention provides a biosensing device to set up the parameters of a strip in the device so that the calibration can be completed at a lower cost and be more user friendly.

BACKGROUND OF THE INVENTION

Biosensing instruments have been developed to detect a variety of biomolecular complexes including oligonucleotides, antibody-antigen interactions, hormone-receptor interactions, and enzyme-substrate interactions. In general, biosensors consist of two components: a highly specific recognition element and a transducer that converts the molecular recognition event into a quantifiable signal. Signal transduction has been accomplished by many methods, including fluorescence and interferometry. Biosensing instruments that employ disposable sample strips enjoy wide consumer acceptance. Such instruments are employed for the detection of analytes such as glucose and cholesterol levels in blood samples and, in general, provide accurate readings.

However, to obtain accurate detecting results, the information in association with the disposable strips (such as calibration parameters, strip type and expiration duration, etc.) must be entered in the biosensing instruments. Calibration of the biosensor must be done first before using it. The strips are different lot by lot. The strip manufacturers must provide the calibration code for each lot of strips. The users must perform a set-up procedure before using the strips according to the manufacturers' manual so that the biosensors can receive correct calibration information. There are two setting procedures known in the art for calibration. One is that the user selects a set of built-in calibration codes in the biosensor according to the corresponding calibration codes marked in the package of the strips. The other is that a code card is attached to each lot of strips in order to save the calibration parameters in a memory unit. In a further calibration of the sensor unit, a parameter setting card corresponding to a lot number of a sensor included therein is inserted into the main unit so that the sensitivity of the equipment is calibrated. In a still further calibration of the sensor unit, correction data is supplied to the main unit in accordance with bar codes labelled thereon to calibrate the sensitivity of the biosensing instrument.

U.S. Pat. No. 4,637,403 provides a hand-held shirt-pocket portable medical diagnostic system for checking measurement of blood glucose, urea nitrogen, hemoglobin, blood components or other body qualities. This prior reference describes an integrated system that provides a method by which the patient lances the finger to get a sample of blood which is then used by the device to provide a reading of the blood glucose or other analyte concentration. This system uses a complex reflectance system to read the analyte level in the sample.

European Patent No. 0351891 describes an electrochemical sensor system and electrodes which are suitable for measuring the concentration of an analyte in a body fluid sample. The system requires the use of expensive electrodes and a reader to determine the analyte concentration level.

U.S. Pat. No. 5,053,199 provides a device including an integrated circuit carrier and a socket for removably and longitudinally receiving the integrated circuit carrier. It describes a biosensing meter with a pluggable memory key. This device uses a pluggable memory key to control the operations of the meter.

U.S. Pat. No. 5,366,609 relates to biosensing meters for determining the presence of an analyte in a biological sample, and, more particularly, to a biosensing meter whose operation is controlled by data accessed from a removably pluggable memory module. It describes a biosensing meter with a pluggable read-only memory wherein data read from the read-only memory at sequential times during the use of the meter enables a determination to be made as to whether the read-only memory has been switched during a test procedure.

Although many improvements have been made, the cost and complexity needed for calibration are still significant. The need to match calibration of a meter to the strips leads to errors in analyte concentration readings. Currently, existing calibration mechanisms require loading a calibration chip or strip, or manually inputting a calibration code into the meter. These devices can be reused numerous times, resulting in errors by the patient who does not change to or enter the appropriate calibration data. An additional issue is the use of test strips which are out of date. Old test strips which are expired can lead to errors and inaccurate results. By providing a means to eliminate the use of expired test strips, the patients will not have to monitor the expiration date of the test strips, and patient errors from using old test strips are eliminated.

There remains an important need to develop rapid, simple, cheaper and reliable calibration for biosensing instruments.

SUMMARY OF THE INVENTION

The invention provides a biosensing device comprising the following units:
- an input unit comprising a parameter-setting card of a strip and a port of the biosensing device wherein the parameter-setting card connects with the port so that the circuit of the card and the signal-acquiring circuit of the biosensor device form a working circuit and produce an electrical signal by providing the circuit with a voltage or a current;
- an analysis unit converting the resulting signal through an analog-to-digital converter (ADC) circuit;
- a process unit decoding the electrical signal obtained from the analysis unit to obtain the data values by pre-defining the maximum value, minimum value and the resolution value to be entered into the biosensing device and determining the minimum unit of measurement from the maximum value and minimum value of the characterizing method; and
- a set unit storing the resulting data values as the basis for calibrating the biosensing device for the strip and giving parameters in the parameter-setting card of the strip to the biosensing device.

DETAILED DESCRIPTION OF THE INVENTION

The invention provides a biosensing device to set up the calibration parameters of the strip in the device so that the calibration can be completed at a lower cost and be more user friendly.

The invention provides a biosensing device comprising the following units:

an input unit comprising a parameter-setting card of a strip and a port of the biosensing device wherein the parameter-setting card connects with the port so that the circuit of the card and the signal-acquiring circuit of the biosensor device form a working circuit and produce an electrical signal by providing the working circuit with a voltage or a current;

an analysis unit converting the resulting signal through an analog-to-digital converter (ADC) circuit;

a process unit decoding the electrical signal obtained from the analysis unit to obtain the data values by pre-defining the maximum value, minimum value and the resolution value to be entered into the biosensing device and determining the minimum unit of measurement from the maximum value and minimum value of the characterizing method; and a set unit storing the resulting data values as the basis for calibrating the biosensing device for the strip or giving the operation-related parameters.

In one embodiment, the invention provides a biosensing device comprising the following units:

(a) an input unit comprising a parameter-setting card of a strip and a port of the biosensing device,
wherein the parameter-setting card comprises a circuit comprised of at least a set of non-memory elements and the port of the biosensing device comprises a signal-acquiring circuit, and wherein the parameter-setting card connects with the port so that the circuit of the card and the signal-acquiring circuit of the biosensor device form a working circuit and produce an electrical signal by providing the circuit on the card with a fixed voltage and the electrical signal ($U_{in}$) is characterized by voltage difference;

(b) an analysis unit converting the resulting electrical signal through an analog-to-digital converter (ADC) circuit;

(c) a process unit decoding the electrical signal obtained from the analysis unit to obtain data values (P),
wherein the data values (P) are obtained by (i) pre-defining maximum value ($P_{max}$), minimum value ($P_{min}$) and resolution value ($P_{res}$) of the biosensing device to obtain data numbers ($P_n$) and (ii) pre-determining the maximum value ($U_{max}$) and minimum value ($U_{min}$) of the voltages of the biosensing device to obtain minimum unit of measurement (step),
wherein the data numbers ($P_n$) is calculated through the following equation:

$$P_n = \frac{P_{max} - P_{min}}{P_{res}},$$

wherein the minimum unit of measurement (step) is calculated through the following equation:

$$\text{step} = \frac{U_{max} - U_{min}}{P_n},$$

and wherein the data values (P) is calculated through the following equation:

$$P = P_{min} + \frac{U_{in} - U_{min}}{\text{step}} \times P_{res};$$

and (d) a set unit storing the resulting data values as the basis for calibrating the biosensing device for the strip, or giving parameters in the parameter-setting card of the strip to the biosensing device.

The biosensing device of the invention comprises four units that set parameters of the device for a strip used therein. The above-mentioned four units are the input unit, analysis unit, process unit and set unit, which are shown in the following scheme:

The input unit of the biosensing device of the invention comprises a parameter-setting card of a strip and a port of the biosensing device wherein the parameter-setting card connects with the port so that the circuit of the card and the signal-acquiring circuit of the biosensing device form a working circuit. In one embodiment, the parameter-setting card comprises a circuit comprised of at least a set of non-memory elements and the port of the biosensing device comprises a signal-acquiring circuit. The parameter-setting card connects with the port so that the circuit of the card and the signal-acquiring circuit of the biosensor device form a working circuit and produce an electrical signal by providing the circuit on the card with a fixed voltage and the electrical signal ($U_{in}$) is characterized by voltage difference (see FIG. 1).

Figure 1:
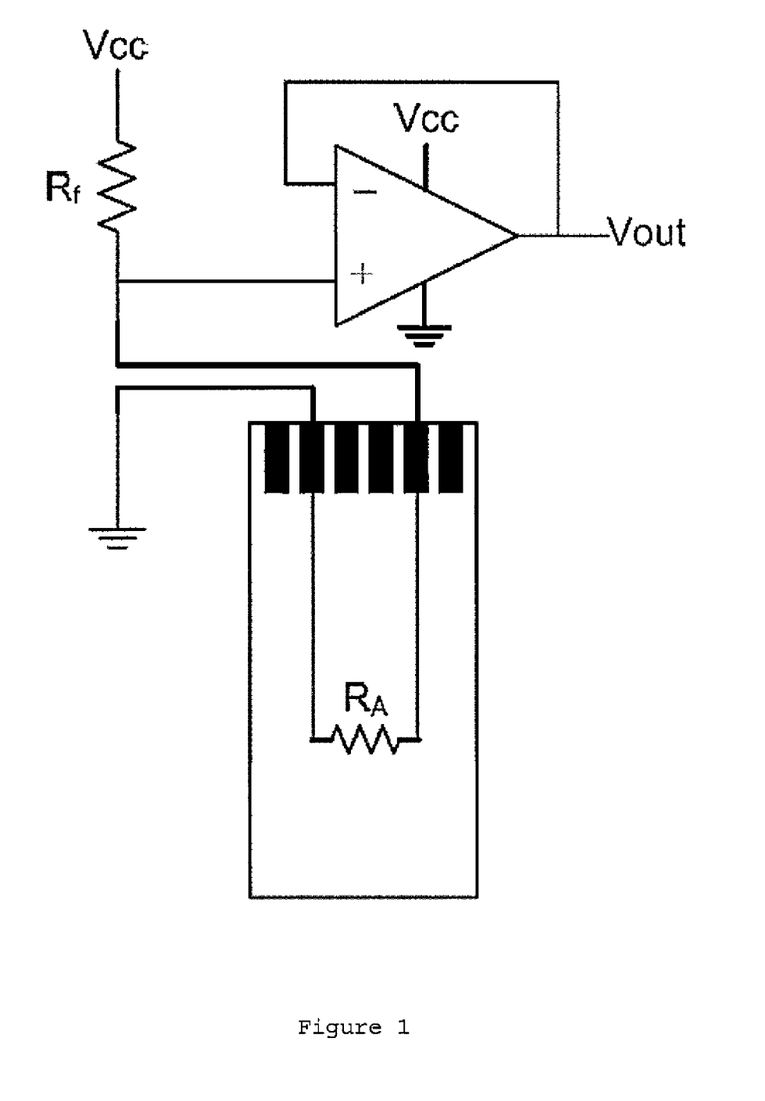
FIG. 1 shows the configuration of the signal-acquiring circuit of the biosensing device and the parameter-setting card of a strip in the input unit of the invention.
Figure 7:
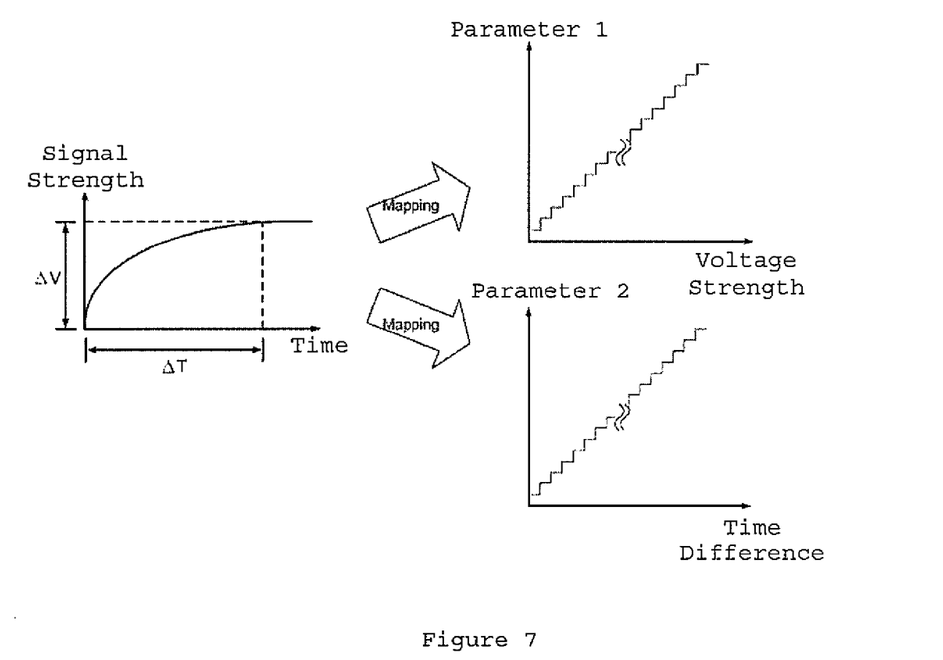
FIG. 7 shows that the setting data can be obtained through the set unit by an encoding and calculation series on the basis of the correspondence between the strength of the voltage or the duration of time and the parameters.
Figure 8:
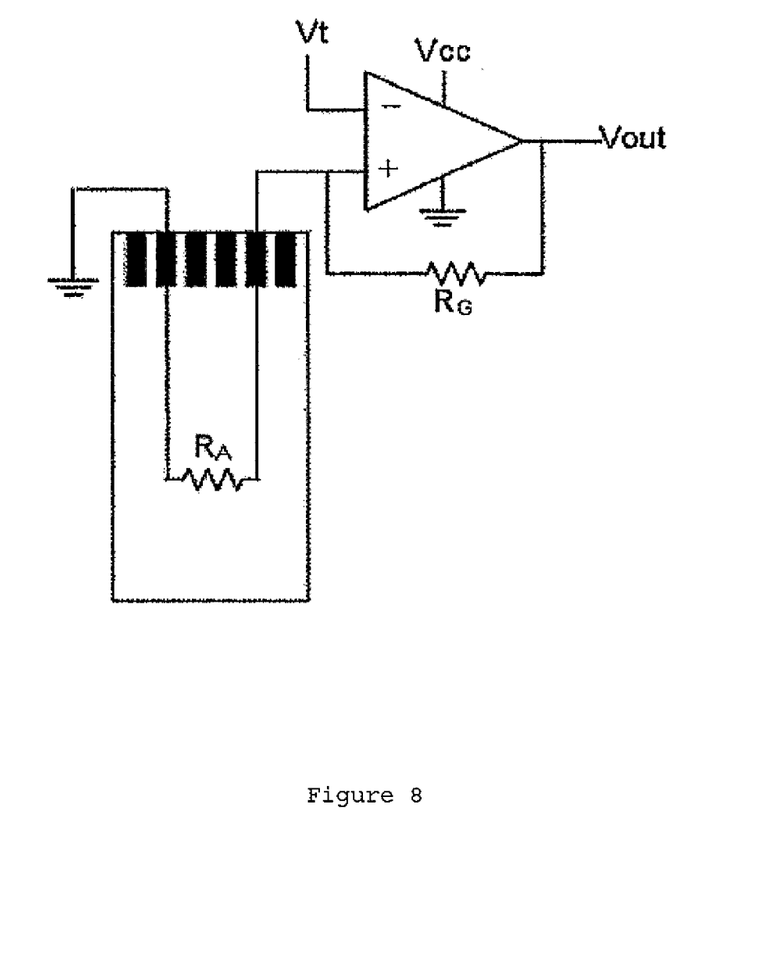
FIG. 8 shows the configuration of the signal-acquiring circuit of the biosensing device and the parameter-setting card of a strip in the input unit of the invention.

The working circuit shown in FIG. 1 is a voltage-to-voltage amplifier that can produce an electrical signal by providing the circuit on the card with a fixed DC (direct current) voltage or a current. The electrical signal can be acquired through the acquiring circuit. When the biosensing device provides a voltage or a current, the circuit on the card produces the electrical signal as the function of time (see FIGS. 2 and 3). The signal is characterized by a voltage difference (ΔV). The provided voltage causes the voltage to change over time to form a voltage-time function. The acquiring circuit can further comprise a multiplexer to select more than one circuit loop to get two or more signals in a parameter setting card (see FIG. 4). The output of signals and its corresponding manner are shown in FIG. 5. Another type of the parameter-setting card can further comprise a capacitor. It provides a signal that varies according to time (e.g. the voltage or current intensity changes over time). On the basis of the voltage difference (ΔV) or time difference (ΔT), the parameter value can be attached to them (see FIG. 7). In addition, the acquiring circuit can be a current-to-voltage amplifier to achieve the same purpose(see FIG. 8). As shown in FIG. 8, the $V_{out}$ depends on $R_A$ with a baseline of $V_t$. The $V_t$ is a DC voltage source. The current which passes through $R_G$ is determined by $R_A$. Since the relationship between $V_{out}$ and $R_A$ is well known, the circuit can be applied to achieve the same purpose as that of FIG. 1. According to the invention, the parameter-setting card comprises an open-loop circuit comprised of at least a set of non-memory elements. The open-loop circuit is preferably the circuit comprised of resistors or capacitors or both in series or parallel configurations. After the parameter-setting card of a strip is inserted into the port of the biosensing device, a working circuit is formed by connecting the signal-acquiring circuit in the port of the biosensing device with the circuit of the parameter-setting card.

The analysis unit of the biosensing device of the invention converts the electrical signal obtained from the input unit through an analog-to-digital converter (ADC) circuit.

The process unit of the biosensing device of the invention encodes the electrical signal obtained from the analysis unit to obtain the data numbers ($P_n$) by pre-defining the maximum value ($P_{max}$), minimum value ($P_{min}$) and the resolution value ($P_{res}$) and determining the minimum unit of measurement from the maximum value and minimum value of the characterizing method. Using the voltage difference as the method to characterize the electrical signal, the data numbers ($P_n$) can be obtained through the following equation:

$$P_n = \frac{P_{max} - P_{min}}{P_{res}} \quad \text{(Eq. 2-1)}$$

In addition, the minimum unit of measurement (step) is determined from the maximum value ($U_{max}$) and the minimum value ($U_{min}$) of the voltages through the following equation:

$$\text{step} = \frac{U_{max} - U_{min}}{P_n}, \quad \text{(Eq. 2-2)}$$

The data values (P) acquired can be calculated by the following equation: (Here $U_{in}$ is the characterized value of signal)

$$P = P_{min} + \frac{U_{in} - U_{min}}{\text{step}} \times P_{res} \quad \text{(Eq. 2-3)}$$

The set unit of the biosensing device of the invention stores the resulting data values as the basis for the calibration of the biosensing device for the strip.

EXAMPLES

Example 1

To enter the slope of the characteristic equation of the strip into the biosensing device, the configuration of the signal-acquiring circuit of the biosensing device and the parameter-setting card of a strip in the input unit of the invention are illustrated in FIG. 1. The signal-acquiring circuit includes at least a reference resistance ($R_f$) and an amplifier circuit. The equivalent impedance ($R_a$) in the reference resistance and the parameter-setting card form a divided circuit. Using the input of the slope of the calibration data as an example, if the slope of the characteristic equation of the strip ranges from 0.5 to 2.0 and the resolution value is 0.02 (e.g., the minimum increment in the range is 0.02), according to Eq. 2-1 stated above, the mapping data number ($P_n$) is as follows:

$$P_n = \frac{P_{max} - P_{min}}{P_{res}} = \frac{2 - 0.5}{0.02} = 75$$

If the ADC reference voltage is 2.5V which is a fixed voltage, the reference resistance ($R_f$) is 10 kΩ and the range of the voltage variation is limited between 0.1 V and 2.5 V, according to Eq. 2-2, the minimum unit of measurement (step) is as follows:

$$\text{step} = \frac{U_{max} - U_{min}}{P_n} = \frac{2.5 - 0.1}{75} = 0.032$$

According to Eq. 2-3, the voltage and their equivalent impedances corresponding to the data values to be entered into the biosensing device can be calculated and determined for implementation of parameter setting card (see Table 1 below). The voltage for each P value (here is slope) can be determined using Eq. 2-3 by algebra method. For example, In the embodiment, for example, the voltage for slop 0.7 can be derive by following equation:

$$0.7 = 0.5 + \frac{Vra - 0.1}{0.032} \times 0.02$$

Vra is 0.420 can be obtained. In addition, the impedance can easy to be calculated by Kirchhoff Circuit Laws. In the embodiment, the reference voltage is set as 2.5 V and the reference resistance is 10 KΩ, so the impedance (Ra) can derived by the equation:

$$Vra = 2.5 \times \frac{RA}{10K\Omega + RA}$$

wherein Vra is the voltage corresponding to slope.

TABLE 1

| slope | $V_{RA}$(V) | Ra(Ω) |
|---|---|---|
| 0.50 | 0.100 | 417 |
| 0.52 | 0.132 | 557 |
| 0.54 | 0.164 | 702 |
| 0.56 | 0.196 | 851 |
| 0.58 | 0.228 | 1004 |

TABLE 1-continued

| slope | $V_{RA}$(V) | Ra(Ω) |
|---|---|---|
| 0.60 | 0.260 | 1161 |
| 0.62 | 0.292 | 1322 |
| 0.64 | 0.324 | 1489 |
| 0.66 | 0.356 | 1660 |
| 0.68 | 0.388 | 1837 |
| 0.70 | 0.420 | 2019 |
| 0.72 | 0.452 | 2207 |
| 0.74 | 0.484 | 2401 |
| 0.76 | 0.516 | 2601 |
| 0.78 | 0.548 | 2807 |
| 0.80 | 0.580 | 3021 |
| 0.82 | 0.612 | 3242 |
| 0.84 | 0.644 | 3470 |
| 0.86 | 0.676 | 3706 |
| 0.88 | 0.708 | 3951 |
| 0.90 | 0.740 | 4205 |
| 0.92 | 0.772 | 4468 |
| 0.94 | 0.804 | 4741 |
| 0.96 | 0.836 | 5024 |
| 0.98 | 0.868 | 5319 |
| 1.00 | 0.900 | 5625 |
| 1.02 | 0.932 | 5944 |
| 1.04 | 0.964 | 6276 |
| 1.06 | 0.996 | 6622 |
| 1.08 | 1.028 | 6984 |
| 1.10 | 1.060 | 7361 |
| 1.12 | 1.092 | 7756 |
| 1.14 | 1.124 | 8169 |
| 1.16 | 1.156 | 8601 |
| 1.18 | 1.188 | 9055 |
| 1.20 | 1.220 | 9531 |
| 1.22 | 1.252 | 10032 |
| 1.24 | 1.284 | 10559 |
| 1.26 | 1.316 | 11115 |
| 1.28 | 1.348 | 11701 |
| 1.30 | 1.380 | 12321 |
| 1.32 | 1.412 | 12978 |
| 1.34 | 1.444 | 13674 |
| 1.36 | 1.476 | 14414 |
| 1.38 | 1.508 | 15202 |
| 1.40 | 1.540 | 16042 |
| 1.42 | 1.572 | 16940 |
| 1.44 | 1.604 | 17902 |
| 1.46 | 1.636 | 18935 |
| 1.48 | 1.668 | 20048 |
| 1.50 | 1.700 | 21250 |
| 1.52 | 1.732 | 22552 |
| 1.54 | 1.764 | 23967 |
| 1.56 | 1.796 | 25511 |
| 1.58 | 1.828 | 27202 |
| 1.60 | 1.860 | 29063 |
| 1.62 | 1.892 | 31118 |
| 1.64 | 1.924 | 33403 |
| 1.66 | 1.956 | 35956 |
| 1.68 | 1.988 | 38828 |
| 1.70 | 2.020 | 42083 |
| 1.72 | 2.052 | 45804 |
| 1.74 | 2.084 | 50096 |
| 1.76 | 2.116 | 55104 |
| 1.78 | 2.148 | 61023 |
| 1.80 | 2.180 | 68125 |
| 1.82 | 2.212 | 76806 |
| 1.84 | 2.244 | 87656 |
| 1.86 | 2.276 | 101607 |
| 1.88 | 2.308 | 120208 |
| 1.90 | 2.340 | 146250 |
| 1.92 | 2.372 | 185313 |
| 1.94 | 2.404 | 250417 |
| 1.96 | 2.436 | 380625 |
| 1.98 | 2.468 | 771250 |
| 2.00 | 2.500 | ∞ |

Figure 2:
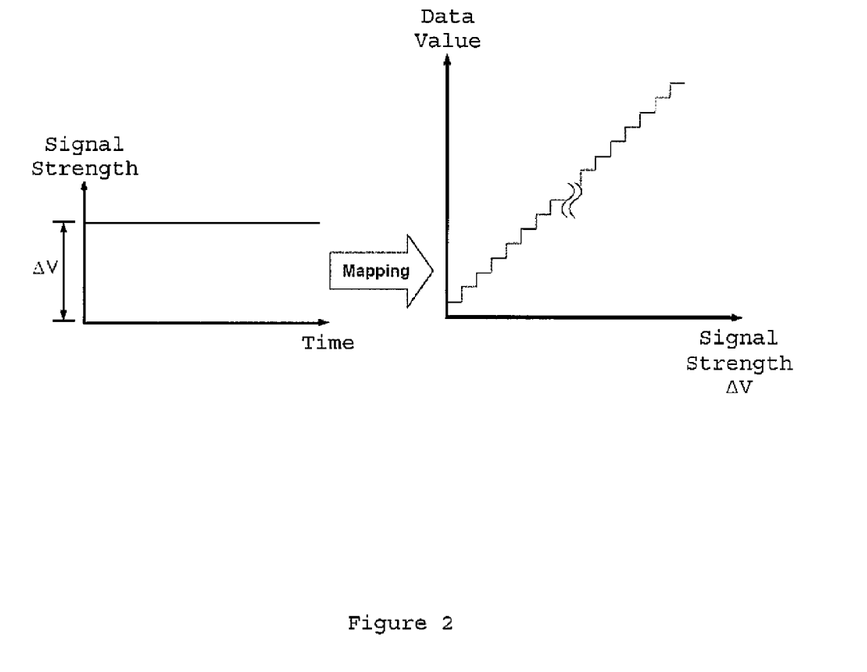
FIG. 2 shows that the encoding method of the invention refers to one parameter in full scale.
Figure 3:
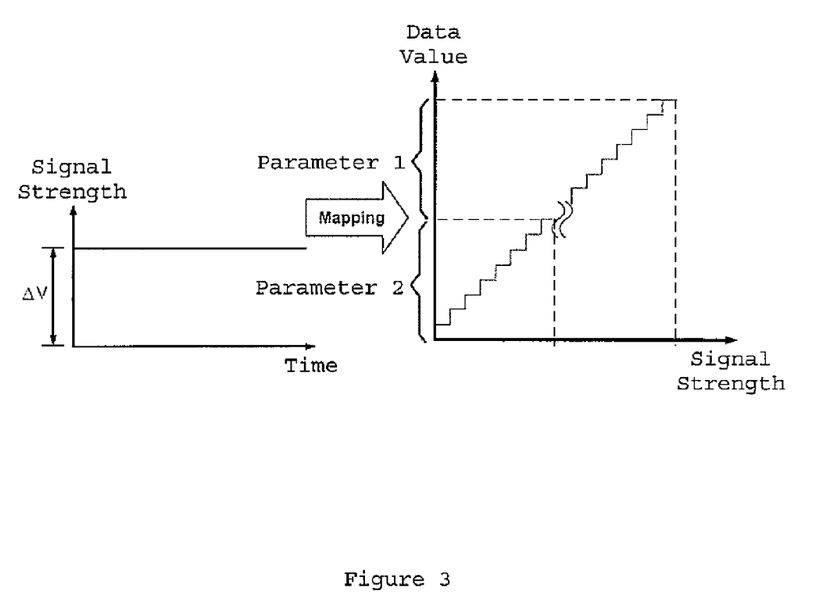
FIG. 3 is a plot expressing the method referring to two or more parameters at one time.

The characterized values of the signal voltage mapping to the slopes can be obtained by pointing out appropriate impedances. By using the amplifier circuit to acquire the signal from the parameter-setting card, the characteristic values can be obtained by the process of the analysis unit. In this example, the characteristic value is the strength of the voltage (ΔV). According to the encoding regulations, the setting data can be obtained through the set unit by an encoding and calculation series on the basis of the strength of the voltage and the corresponding parameters. FIG. 2 shows that the above-mentioned encoding method can also be changed to that referring to two or more parameters at one time, which can be used in a different data type that does not need to be entered for the same setting. FIG. 3 is a plot expressing the method referring to two or more parameters at one time.

Example 2

Figure 4:
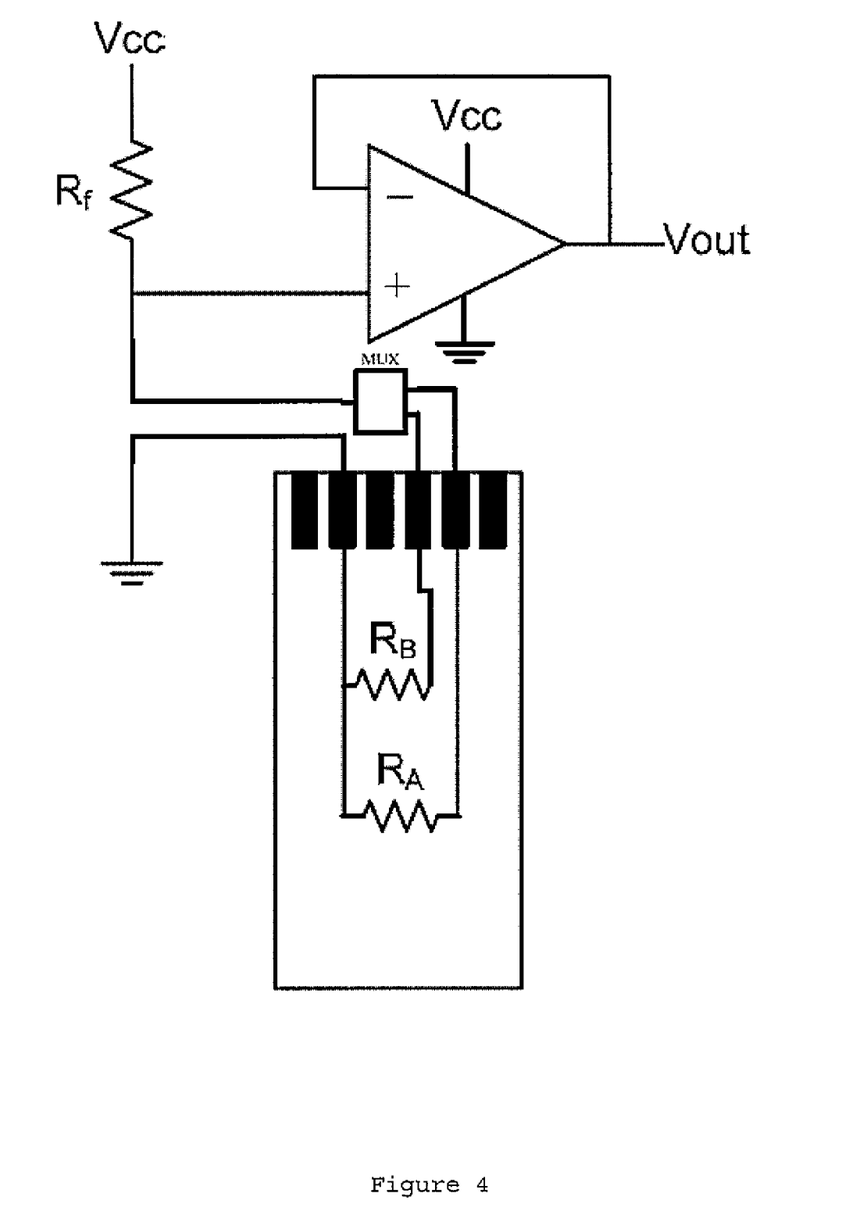
FIG. 4 shows the configuration of the signal-acquiring circuit of the biosensing device and the parameter-setting card of a strip in the input unit of the invention.
Figure 5:
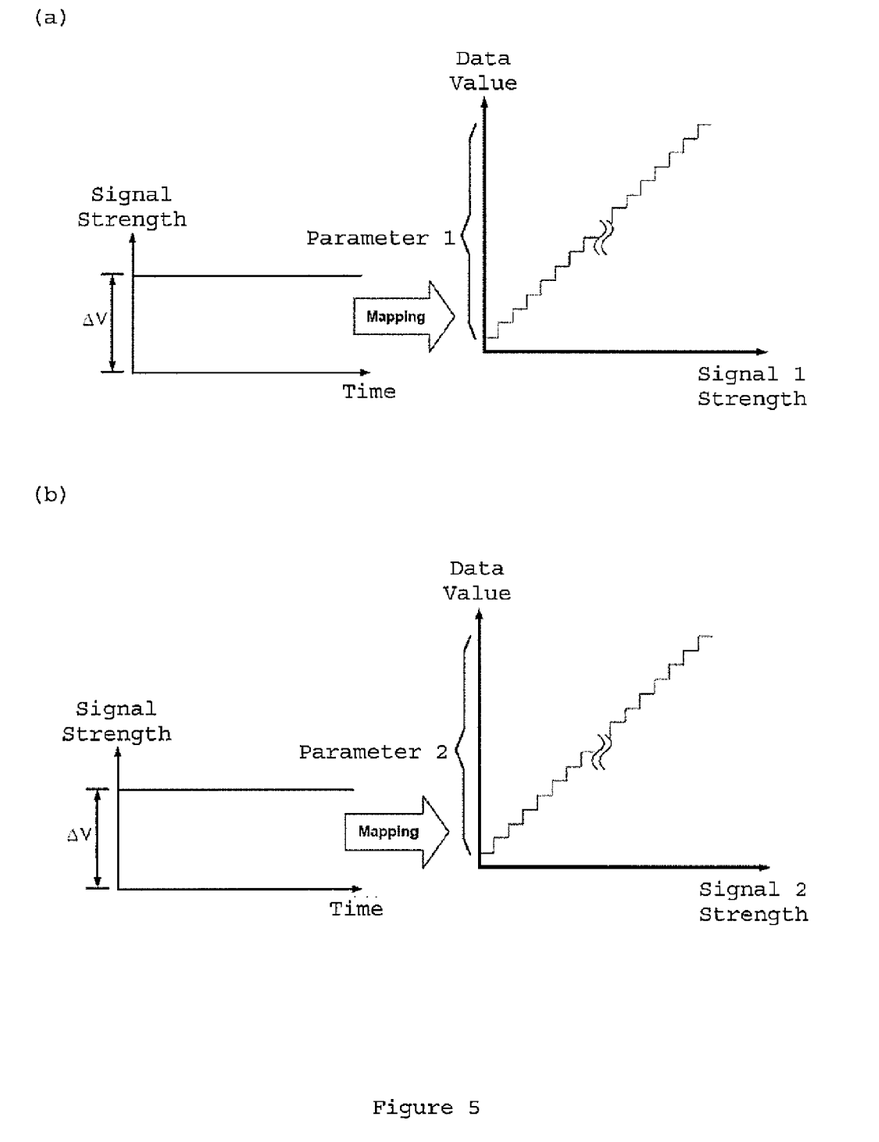
FIG. 5 shows that the setting data can be obtained through the set unit by an encoding and calculation series on the basis of the strength of the voltage and the corresponding parameters.

If the slope and intercept of the characteristic equation of the strip are entered into the biosensing device simultaneously, the configuration of the signal-acquiring circuit of the biosensing device and the parameter-setting card of a strip in the input unit of the invention are as illustrated in FIG. 4. The signal-acquiring circuit includes at least a reference resistance ($R_f$), an amplifier circuit and a signal selection circuit (for example, a multiplexer). By changing the signal through the signal selection circuit, the equivalent impedance ($R_a$ or $R_b$) in the parameter-setting card and the reference resistance forms a divided circuit, wherein the circuit of Ra is the signal corresponding to the slope of the parameter for setting and the circuit of Rb is the signal corresponding to the intercept of the parameter for setting. If the slope of the characteristic equation of the strip ranges from 0.5 to 2.0 and the resolution value is 0.02, the mapping way is as shown in Example 1 above. In addition, the intercept may range from 0.1 V to 0.5 V and its resolution value is 0.005. According to Eq. 2-1 stated above, the mapping data number ($P_n$) is as follows:

$$P_n = \frac{P_{max} - P_{min}}{P_{res}} = \frac{0.5 - 0.1}{0.005} = 80$$

If the ADC reference voltage is 2.5V, the reference resistance ($R_f$) is 10 kΩ and the range of the voltage variation is limited between 0.1 and 2.5, according to Eq. 2-2, the minimum unit of measurement (step) is as follows:

$$step = \frac{U_{max} - U_{min}}{P_n} = \frac{2.5 - 0.1}{80} = 0.03$$

According to Eq. 2-3, the voltage values and their equivalent impedances corresponding to the data values to be entered into the biosensing device can be calculated (see Table 2 below).

TABLE 2

| Intercept | $V_{Rb}$(V) | Rb (Ω) |
|---|---|---|
| 0.100 | 0.100 | 417 |
| 0.105 | 0.130 | 438 |
| 0.110 | 0.160 | 460 |
| 0.115 | 0.190 | 482 |
| 0.120 | 0.220 | 504 |
| 0.125 | 0.250 | 526 |
| 0.130 | 0.280 | 549 |
| 0.135 | 0.310 | 571 |
| 0.140 | 0.340 | 593 |
| 0.145 | 0.370 | 616 |
| 0.150 | 0.400 | 638 |
| 0.155 | 0.430 | 661 |

TABLE 2-continued

| Intercept | $V_{Rb}$ (V) | Rb (Ω) |
|---|---|---|
| 0.160 | 0.460 | 684 |
| 0.165 | 0.490 | 707 |
| 0.170 | 0.520 | 730 |
| 0.175 | 0.550 | 753 |
| 0.180 | 0.580 | 776 |
| 0.185 | 0.610 | 799 |
| 0.190 | 0.640 | 823 |
| 0.195 | 0.670 | 846 |
| 0.200 | 0.700 | 870 |
| 0.205 | 0.730 | 893 |
| 0.210 | 0.760 | 917 |
| 0.215 | 0.790 | 941 |
| 0.220 | 0.820 | 965 |
| 0.225 | 0.850 | 989 |
| 0.230 | 0.880 | 1013 |
| 0.235 | 0.910 | 1038 |
| 0.240 | 0.940 | 1062 |
| 0.245 | 0.970 | 1086 |
| 0.250 | 1.000 | 6667 |
| 0.255 | 1.030 | 7007 |
| 0.260 | 1.060 | 7361 |
| 0.265 | 1.090 | 7730 |
| 0.270 | 1.120 | 8116 |
| 0.275 | 1.150 | 8519 |
| 0.280 | 1.180 | 8939 |
| 0.285 | 1.210 | 9380 |
| 0.290 | 1.240 | 9841 |
| 0.295 | 1.270 | 10325 |
| 0.300 | 1.300 | 10833 |
| 0.305 | 1.330 | 11368 |
| 0.310 | 1.360 | 11930 |
| 0.315 | 1.390 | 12523 |
| 0.320 | 1.420 | 13148 |
| 0.325 | 1.450 | 13810 |
| 0.330 | 1.480 | 14510 |
| 0.335 | 1.510 | 15253 |
| 0.340 | 1.540 | 16042 |
| 0.345 | 1.570 | 16882 |
| 0.350 | 1.600 | 17778 |
| 0.355 | 1.630 | 18736 |
| 0.360 | 1.660 | 19762 |
| 0.365 | 1.690 | 20864 |
| 0.370 | 1.720 | 22051 |
| 0.375 | 1.750 | 23333 |
| 0.380 | 1.780 | 24722 |
| 0.385 | 1.810 | 26232 |
| 0.390 | 1.840 | 27879 |
| 0.395 | 1.870 | 29683 |
| 0.400 | 1.900 | 31667 |
| 0.405 | 1.930 | 33860 |
| 0.410 | 1.960 | 36296 |
| 0.415 | 1.990 | 39020 |
| 0.420 | 2.020 | 42083 |
| 0.425 | 2.050 | 45556 |
| 0.430 | 2.080 | 49524 |
| 0.435 | 2.110 | 54103 |
| 0.440 | 2.140 | 59444 |
| 0.445 | 2.170 | 65758 |
| 0.450 | 2.200 | 73333 |
| 0.455 | 2.230 | 82593 |
| 0.460 | 2.260 | 94167 |
| 0.465 | 2.290 | 109048 |
| 0.470 | 2.320 | 128889 |
| 0.475 | 2.350 | 156667 |
| 0.480 | 2.38 | 198333 |
| 0.485 | 2.41 | 267778 |
| 0.490 | 2.44 | 406667 |
| 0.495 | 2.47 | 823333 |
| 0.500 | 2.50 | ∞ |

The characterized values of the signal voltage mapping to the slopes can be obtained by pointing out appropriate impedances. By controlling the signal selection circuit, $R_a$, the reference resistance and the biosensing device can form the signal wave shape of the circuit output. The slope can be obtained by using the amplifier circuit to acquire the signal from the parameter-setting card and encoding the resulting data. After completion, Rb was chosen as the working resistance by the signal selection circuit, Ra exhibited an open-loop state and the signal generated on the basis of Rb was acquired by using the amplifier circuit, and the characteristic value of the strength of the voltage ($\Delta V$) can be obtained by the process of the analysis unit. According to the encoding regulations, the setting data can be obtained through the set unit by an encoding and calculation series on the basis of the strength of the voltage and the corresponding parameters (see FIG. 5).

Example 3

Figure 6:
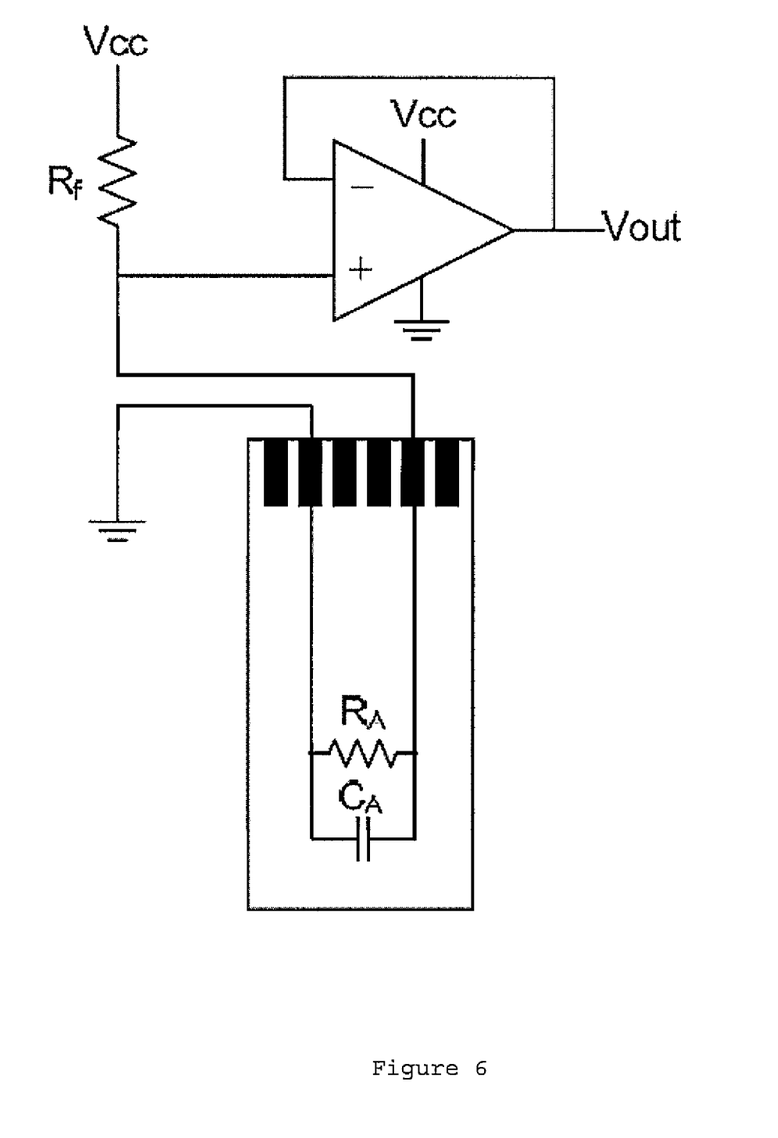
FIG. 6 shows the configuration of the signal-acquiring circuit of the biosensing device and the parameter-setting card of a strip in the input unit of the invention.

The manufacturing date of a strip can be entered into the biosensing device to manage the expiration date of the strip. The characteristic methods of the invention can represent year and week numbers. The configuration of the circuit of the biosensing device and the parameter-setting card of a strip in the input unit of the invention are illustrated in FIG. 6. The signal-acquiring circuit includes at least a reference resistance ($R_f$) and an amplifier circuit. The reference resistance and the impedances that are $R_a$ and $C_A$ in parallel in the parameter-setting card form a divided circuit. The equivalent impedance in the parameter-setting card changes depending on the parameters. Since the $C_A$ is a component with the function of time or frequency, the voltage strength ($\Delta V$) and time difference ($\Delta T$) can both be applied to decode for parameter inputting. By using the amplifier circuit to acquire the signal from the parameter-setting card, the characteristic value of the signal wave shape can be obtained by the process of the analysis unit. In this example, the characteristic values are the strength of the voltage ($\Delta V$) and the time difference ($\Delta T$). According to the encoding regulations, the setting data can be obtained through the set unit by an encoding and calculation series on the basis of the strength of the voltage and the corresponding parameters (see FIG. 7).

For example, if each week from 2007 to 2011 is to be entered into the biosensing device, the characteristic values are the voltage strength ($\Delta V$) and time difference ($\Delta T$), which represent week numbers and year, respectively. For the encoding of week numbers, since a year includes 52 weeks, the mapping data number ($P_n$) according to Eq. 2-1 is as follows:

$$P_n = \frac{P_{max} - P_{min}}{P_{res}} = \frac{52 - 1}{1} = 51$$

If the ADC reference voltage is 2.5V, the reference resistance ($R_f$) is 470 kΩ and the range of the voltage variation is limited between 0.2 V and 1.73 V, according to Eq. 2-2, the minimum unit of measurement (step) is as follows:

$$\text{step} = \frac{U_{max} - U_{min}}{P_n} = \frac{1.73 - 0.2}{51} = 0.03$$

According to Eq. 2-3, the voltage values and their equivalent impedances corresponding to the data values to be entered into the biosensing device can be calculated (see Table 3 below).

TABLE 3

| | Year | | | | | | | | | | | |
|---|---|---|---|---|---|---|---|---|---|---|---|---|
| | 2007 ΔT = 0.5 s | | | | 2008 ΔT = 0.4 s | | | | 2009 ΔT = 0.3 s | | | |
| weak | Vra (ΔV) | time const. | $R_a$ (Ω) | Ca (uF) | VRa (ΔV) | time const. | $R_a$ (Ω) | Ca (uF) | VRa (ΔV) | time const. | $R_a$ (Ω) | Ca (uF) |
| 1 | 0.200 | 0.102 | 40870 | 2.70 | 0.200 | 0.083 | 40870 | 2.200 | 0.200 | 0.056 | 40870 | 1.500 |
| 2 | 0.230 | 0.095 | 47621 | 2.20 | 0.230 | 0.078 | 47621 | 1.800 | 0.230 | 0.065 | 47621 | 1.500 |
| 3 | 0.260 | 0.098 | 54554 | 2.00 | 0.260 | 0.073 | 54554 | 1.500 | 0.260 | 0.059 | 54554 | 1.200 |
| 4 | 0.290 | 0.098 | 61674 | 1.80 | 0.290 | 0.082 | 61674 | 1.500 | 0.290 | 0.065 | 61674 | 1.200 |
| 5 | 0.320 | 0.096 | 68991 | 1.60 | 0.320 | 0.072 | 68991 | 1.200 | 0.320 | 0.060 | 68991 | 1.000 |
| 6 | 0.350 | 0.099 | 76512 | 1.50 | 0.350 | 0.079 | 76512 | 1.200 | 0.350 | 0.066 | 76512 | 1.000 |
| 7 | 0.380 | 0.107 | 84245 | 1.50 | 0.380 | 0.086 | 84245 | 1.200 | 0.380 | 0.059 | 84245 | 0.820 |
| 8 | 0.410 | 0.092 | 92201 | 1.20 | 0.410 | 0.077 | 92201 | 1.000 | 0.410 | 0.063 | 92201 | 0.820 |
| 9 | 0.440 | 0.099 | 100388 | 1.20 | 0.440 | 0.083 | 100388 | 1.000 | 0.440 | 0.056 | 100388 | 0.680 |
| 10 | 0.470 | 0.106 | 108818 | 1.20 | 0.470 | 0.072 | 108818 | 0.820 | 0.470 | 0.060 | 108818 | 0.680 |
| 11 | 0.500 | 0.094 | 117500 | 1.00 | 0.500 | 0.077 | 117500 | 0.820 | 0.500 | 0.064 | 117500 | 0.680 |
| 12 | 0.530 | 0.100 | 126447 | 1.00 | 0.530 | 0.082 | 126447 | 0.820 | 0.530 | 0.056 | 126447 | 0.560 |
| 13 | 0.560 | 0.105 | 135670 | 1.00 | 0.560 | 0.086 | 135670 | 0.820 | 0.560 | 0.059 | 135670 | 0.560 |
| 14 | 0.590 | 0.091 | 145183 | 0.82 | 0.590 | 0.075 | 145183 | 0.680 | 0.590 | 0.062 | 145183 | 0.560 |
| 15 | 0.620 | 0.096 | 155000 | 0.82 | 0.620 | 0.079 | 155000 | 0.680 | 0.620 | 0.065 | 155000 | 0.560 |
| 16 | 0.650 | 0.100 | 165135 | 0.82 | 0.650 | 0.083 | 165135 | 0.680 | 0.650 | 0.057 | 165135 | 0.470 |
| 17 | 0.680 | 0.105 | 175604 | 0.82 | 0.680 | 0.087 | 175604 | 0.680 | 0.680 | 0.060 | 175604 | 0.470 |
| 18 | 0.710 | 0.091 | 186425 | 0.68 | 0.710 | 0.075 | 186425 | 0.560 | 0.710 | 0.063 | 186425 | 0.470 |
| 19 | 0.740 | 0.095 | 197614 | 0.68 | 0.740 | 0.078 | 197614 | 0.560 | 0.740 | 0.065 | 197614 | 0.470 |
| 20 | 0.770 | 0.098 | 209191 | 0.68 | 0.770 | 0.081 | 209191 | 0.560 | 0.770 | 0.056 | 209191 | 0.390 |
| 21 | 0.800 | 0.102 | 221176 | 0.68 | 0.800 | 0.084 | 221176 | 0.560 | 0.800 | 0.059 | 221176 | 0.390 |
| 22 | 0.830 | 0.106 | 233593 | 0.68 | 0.830 | 0.073 | 233593 | 0.470 | 0.830 | 0.061 | 233593 | 0.390 |
| 23 | 0.860 | 0.091 | 246463 | 0.56 | 0.860 | 0.076 | 246463 | 0.470 | 0.860 | 0.063 | 246463 | 0.390 |
| 24 | 0.890 | 0.094 | 259814 | 0.56 | 0.890 | 0.079 | 259814 | 0.470 | 0.890 | 0.055 | 259814 | 0.330 |
| 25 | 0.920 | 0.097 | 273671 | 0.56 | 0.920 | 0.081 | 273671 | 0.470 | 0.920 | 0.057 | 273671 | 0.330 |
| 26 | 0.950 | 0.100 | 288065 | 0.56 | 0.950 | 0.084 | 288065 | 0.470 | 0.950 | 0.059 | 288065 | 0.330 |
| 27 | 0.980 | 0.103 | 303026 | 0.56 | 0.980 | 0.087 | 303026 | 0.470 | 0.980 | 0.061 | 303026 | 0.330 |
| 28 | 1.010 | 0.106 | 318591 | 0.56 | 1.010 | 0.074 | 318591 | 0.390 | 1.010 | 0.063 | 318591 | 0.330 |
| 29 | 1.040 | 0.092 | 334795 | 0.47 | 1.040 | 0.076 | 334795 | 0.390 | 1.040 | 0.065 | 334795 | 0.330 |
| 30 | 1.070 | 0.095 | 351678 | 0.47 | 1.070 | 0.078 | 351678 | 0.390 | 1.070 | 0.054 | 351678 | 0.270 |
| 31 | 1.100 | 0.097 | 369286 | 0.47 | 1.100 | 0.081 | 369286 | 0.390 | 1.100 | 0.056 | 369286 | 0.270 |
| 32 | 1.130 | 0.100 | 387664 | 0.47 | 1.130 | 0.083 | 387664 | 0.390 | 1.130 | 0.057 | 387664 | 0.270 |
| 33 | 1.160 | 0.102 | 406866 | 0.47 | 1.160 | 0.085 | 406866 | 0.390 | 1.160 | 0.059 | 406866 | 0.270 |
| 34 | 1.190 | 0.105 | 426947 | 0.47 | 1.190 | 0.074 | 426947 | 0.330 | 1.190 | 0.060 | 426947 | 0.270 |
| 35 | 1.220 | 0.094 | 447969 | 0.41 | 1.220 | 0.076 | 447969 | 0.330 | 1.220 | 0.062 | 447969 | 0.270 |
| 36 | 1.250 | 0.096 | 470000 | 0.41 | 1.250 | 0.078 | 470000 | 0.330 | 1.250 | 0.063 | 470000 | 0.270 |
| 37 | 1.280 | 0.099 | 493115 | 0.41 | 1.280 | 0.079 | 493115 | 0.330 | 1.280 | 0.065 | 493115 | 0.270 |
| 38 | 1.310 | 0.101 | 517395 | 0.41 | 1.310 | 0.081 | 517395 | 0.330 | 1.310 | 0.054 | 517395 | 0.220 |
| 39 | 1.340 | 0.098 | 542931 | 0.39 | 1.340 | 0.083 | 542931 | 0.330 | 1.340 | 0.055 | 542931 | 0.220 |
| 40 | 1.370 | 0.100 | 569823 | 0.39 | 1.370 | 0.085 | 569823 | 0.330 | 1.370 | 0.057 | 569823 | 0.220 |
| 41 | 1.400 | 0.103 | 598182 | 0.39 | 1.400 | 0.087 | 598182 | 0.330 | 1.400 | 0.058 | 598182 | 0.220 |
| 42 | 1.430 | 0.105 | 628131 | 0.39 | 1.430 | 0.073 | 628131 | 0.270 | 1.430 | 0.059 | 628131 | 0.220 |
| 43 | 1.460 | 0.107 | 659808 | 0.39 | 1.460 | 0.074 | 659808 | 0.270 | 1.460 | 0.060 | 659808 | 0.220 |
| 44 | 1.490 | 0.092 | 693366 | 0.33 | 1.490 | 0.076 | 693366 | 0.270 | 1.490 | 0.062 | 693366 | 0.220 |
| 45 | 1.520 | 0.094 | 728980 | 0.33 | 1.520 | 0.077 | 728980 | 0.270 | 1.520 | 0.063 | 728980 | 0.220 |
| 46 | 1.550 | 0.096 | 766842 | 0.33 | 1.550 | 0.079 | 766842 | 0.270 | 1.550 | 0.064 | 766842 | 0.220 |
| 47 | 1.580 | 0.098 | 807174 | 0.33 | 1.580 | 0.080 | 807174 | 0.270 | 1.580 | 0.065 | 807174 | 0.220 |
| 48 | 1.610 | 0.100 | 850225 | 0.33 | 1.610 | 0.082 | 850225 | 0.270 | 1.610 | 0.054 | 850225 | 0.180 |
| 49 | 1.640 | 0.102 | 896279 | 0.33 | 1.640 | 0.083 | 896279 | 0.270 | 1.640 | 0.055 | 896279 | 0.180 |
| 50 | 1.670 | 0.104 | 945663 | 0.33 | 1.670 | 0.085 | 945663 | 0.270 | 1.670 | 0.057 | 945663 | 0.180 |
| 51 | 1.700 | 0.096 | 998750 | 0.30 | 1.700 | 0.086 | 998750 | 0.270 | 1.700 | 0.058 | 998750 | 0.180 |
| 52 | 1.730 | 0.098 | 1055974 | 0.30 | 1.730 | 0.088 | 1055974 | 0.270 | 1.730 | 0.059 | 1055974 | 0.180 |

| | Year | | | | | | | |
|---|---|---|---|---|---|---|---|---|
| | 2010 ΔT = 0.2 s | | | | 2011 ΔT = 0.1 s | | | |
| weak | VRa (ΔV) | time const. | $R_a$ (Ω) | Ca (uF) | VRa (ΔV) | time const. | $R_a$ (Ω) | Ca (uF) |
| 1 | 0.200 | 0.038 | 40870 | 1.000 | 0.200 | 0.021 | 40870 | 0.560 |
| 2 | 0.230 | 0.043 | 47621 | 1.000 | 0.230 | 0.020 | 47621 | 0.470 |
| 3 | 0.260 | 0.040 | 54554 | 0.820 | 0.260 | 0.019 | 54554 | 0.390 |
| 4 | 0.290 | 0.037 | 61674 | 0.680 | 0.290 | 0.021 | 61674 | 0.390 |
| 5 | 0.320 | 0.041 | 68991 | 0.680 | 0.320 | 0.020 | 68991 | 0.330 |
| 6 | 0.350 | 0.037 | 76512 | 0.560 | 0.350 | 0.022 | 76512 | 0.330 |
| 7 | 0.380 | 0.040 | 84245 | 0.560 | 0.380 | 0.019 | 84245 | 0.270 |
| 8 | 0.410 | 0.043 | 92201 | 0.560 | 0.410 | 0.021 | 92201 | 0.270 |
| 9 | 0.440 | 0.039 | 100388 | 0.470 | 0.440 | 0.018 | 100388 | 0.220 |
| 10 | 0.470 | 0.042 | 108818 | 0.470 | 0.470 | 0.019 | 108818 | 0.220 |
| 11 | 0.500 | 0.037 | 117500 | 0.390 | 0.500 | 0.021 | 117500 | 0.220 |
| 12 | 0.530 | 0.039 | 126447 | 0.390 | 0.530 | 0.022 | 126447 | 0.220 |
| 13 | 0.560 | 0.041 | 135670 | 0.390 | 0.560 | 0.019 | 135670 | 0.180 |

TABLE 3-continued

| | | | | | | | | |
|---|---|---|---|---|---|---|---|---|
| 14 | 0.590 | 0.043 | 145183 | 0.390 | 0.590 | 0.020 | 145183 | 0.180 |
| 15 | 0.620 | 0.038 | 155000 | 0.330 | 0.620 | 0.021 | 155000 | 0.180 |
| 16 | 0.650 | 0.040 | 165135 | 0.330 | 0.650 | 0.018 | 165135 | 0.150 |
| 17 | 0.680 | 0.042 | 175604 | 0.330 | 0.680 | 0.019 | 175604 | 0.150 |
| 18 | 0.710 | 0.044 | 186425 | 0.330 | 0.710 | 0.020 | 186425 | 0.150 |
| 19 | 0.740 | 0.038 | 197614 | 0.270 | 0.740 | 0.021 | 197614 | 0.150 |
| 20 | 0.770 | 0.039 | 209191 | 0.270 | 0.770 | 0.022 | 209191 | 0.150 |
| 21 | 0.800 | 0.041 | 221176 | 0.270 | 0.800 | 0.018 | 221176 | 0.120 |
| 22 | 0.830 | 0.042 | 233593 | 0.270 | 0.830 | 0.019 | 233593 | 0.120 |
| 23 | 0.860 | 0.044 | 246463 | 0.270 | 0.860 | 0.019 | 246463 | 0.120 |
| 24 | 0.890 | 0.037 | 259814 | 0.220 | 0.890 | 0.020 | 259814 | 0.120 |
| 25 | 0.920 | 0.038 | 273671 | 0.220 | 0.920 | 0.021 | 273671 | 0.120 |
| 26 | 0.950 | 0.039 | 288065 | 0.220 | 0.950 | 0.021 | 288065 | 0.120 |
| 27 | 0.980 | 0.041 | 303026 | 0.220 | 0.980 | 0.018 | 303026 | 0.100 |
| 28 | 1.010 | 0.042 | 318591 | 0.220 | 1.010 | 0.019 | 318591 | 0.100 |
| 29 | 1.040 | 0.043 | 334795 | 0.220 | 1.040 | 0.020 | 334795 | 0.100 |
| 30 | 1.070 | 0.036 | 351678 | 0.180 | 1.070 | 0.020 | 351678 | 0.100 |
| 31 | 1.100 | 0.037 | 369286 | 0.180 | 1.100 | 0.021 | 369286 | 0.100 |
| 32 | 1.130 | 0.038 | 387664 | 0.180 | 1.130 | 0.021 | 387664 | 0.100 |
| 33 | 1.160 | 0.039 | 406866 | 0.180 | 1.160 | 0.022 | 406866 | 0.100 |
| 34 | 1.190 | 0.040 | 426947 | 0.180 | 1.190 | 0.018 | 426947 | 0.082 |
| 35 | 1.220 | 0.041 | 447969 | 0.180 | 1.220 | 0.019 | 447969 | 0.082 |
| 36 | 1.250 | 0.042 | 470000 | 0.180 | 1.250 | 0.019 | 470000 | 0.082 |
| 37 | 1.280 | 0.043 | 493115 | 0.180 | 1.280 | 0.020 | 493115 | 0.082 |
| 38 | 1.310 | 0.037 | 517395 | 0.150 | 1.310 | 0.020 | 517395 | 0.082 |
| 39 | 1.340 | 0.038 | 542931 | 0.150 | 1.340 | 0.021 | 542931 | 0.082 |
| 40 | 1.370 | 0.039 | 569823 | 0.150 | 1.370 | 0.021 | 569823 | 0.082 |
| 41 | 1.400 | 0.039 | 598182 | 0.150 | 1.400 | 0.022 | 598182 | 0.082 |
| 42 | 1.430 | 0.040 | 628131 | 0.150 | 1.430 | 0.018 | 628131 | 0.068 |
| 43 | 1.460 | 0.041 | 659808 | 0.150 | 1.460 | 0.019 | 659808 | 0.068 |
| 44 | 1.490 | 0.042 | 693366 | 0.150 | 1.490 | 0.019 | 693366 | 0.068 |
| 45 | 1.520 | 0.043 | 728980 | 0.150 | 1.520 | 0.019 | 728980 | 0.068 |
| 46 | 1.550 | 0.044 | 766842 | 0.150 | 1.550 | 0.020 | 766842 | 0.068 |
| 47 | 1.580 | 0.045 | 807174 | 0.150 | 1.580 | 0.020 | 807174 | 0.068 |
| 48 | 1.610 | 0.036 | 850225 | 0.120 | 1.610 | 0.021 | 850225 | 0.068 |
| 49 | 1.640 | 0.037 | 896279 | 0.120 | 1.640 | 0.021 | 896279 | 0.068 |
| 50 | 1.670 | 0.038 | 945663 | 0.120 | 1.670 | 0.021 | 945663 | 0.068 |
| 51 | 1.700 | 0.038 | 998750 | 0.120 | 1.700 | 0.022 | 998750 | 0.068 |
| 52 | 1.730 | 0.039 | 1055974 | 0.120 | 1.730 | 0.018 | 1055974 | 0.056 |

In addition, for the encoding of year, since the years to be entered range from 2007 to 2012, according to Eq. 2-1, the mapping data number ($P_n$) according to Eq. 2-1 is as follows:

$$P_n = \frac{P_{max} - P_{min}}{P_{res}} = \frac{2011 - 2007}{1} = 4.$$

If the ADC reference voltage is 2.5V, the reference resistance ($R_f$) is 470 kΩ and the range of the time reference (ΔT) variation is limited between 0.5 and 0.1, according to Eq. 2-2, the minimum unit of measurement (step) is as follows:

$$\text{step} = \frac{U_{max} - U_{min}}{P_n} = \frac{0.5 - 0.1}{4} = 0.1$$

According to Eq. 2-3, the time difference (ΔT) and the equivalent capacitance value ($C_A$) corresponding to the data values to be entered into the biosensing device can be calculated (see Table 3 above).

What is claimed is:

1. A biosensing device comprising the following units:
(a) an input unit comprising a parameter-setting card of a strip and a port of the biosensing device,
wherein the parameter-setting card comprises a circuit comprised of at least a set of non-memory elements and the port of the biosensing device comprises a signal-acquiring circuit, wherein the circuit inside the parameter-setting card is comprised of a combination of resistors and capacitors, or a combination of resistors and inductors, and the resistors, the capacitors and the inductors are positioned in series or parallel configurations, and wherein the parameter-setting card connects with the port so that the circuit of the card and the signal-acquiring circuit of the biosensor device form a working circuit and produce an electrical signal by providing the circuit on the card with a fixed voltage and the electrical signal comprises at least one characteristic value ($U_{in}$) being voltage difference, time difference or a combination of the two;

(b) an analysis unit converting the resulting electrical signal through an analog-to-digital converter (ADC) circuit;

(c) a process unit programmed to decode the electrical signal, wherein the electrical signal comprises at least one characteristic value obtained from the analysis unit to obtain at least one data value (P),
wherein the data value (P) is obtained by (i) pre-defining maximum value ($P_{max}$), minimum value ($P_{min}$) and resolution value ($P_{res}$) of the biosensing device to obtain data number ($P_n$) and (ii) pre-determining the maximum value ($U_{max}$) and minimum value ($U_{min}$) of the voltages and/or time of the biosensing device to obtain minimum unit of measurement (step),
wherein the data number ($P_n$) is calculated through the following equation:

$$P_n = \frac{P_{max} - P_{min}}{P_{res}},$$

wherein the minimum unit of measurement (step) is calculated through the following equation:

$$step = \frac{U_{max} - U_{min}}{P_n},$$

and wherein the data value (P) is calculated through the following equation:

$$P = P_{min} + \frac{U_{in} - U_{min}}{step} \times P_{res};$$

and
(d) a set unit storing the resulting at least one data value as the basis for calibrating the biosensing device for the strip, or giving at least one parameter in the parameter-setting card of the strip to the biosensing device.

2. The biosensing device according to claim 1, wherein the voltage that provides the circuit of the card is a DC (direct current) electric source.

3. The biosensing device according to claim 2, wherein the electric source is built into the biosensing device.

* * * * *